12) United States Patent
Saintigny et al.

(10) Patent No.: US 9,410,152 B2
(45) Date of Patent: Aug. 9, 2016

(54) USE OF MICRORNA MOLECULES TO INFLUENCE SKIN PIGMENTATION

(71) Applicants: Gaelle Saintigny, Paris (FR); Christian Mahe, Neuilly sur Seine (FR); Lionel Larue, Bures sur Yvette (FR); Florian Rambow, Antony (FR)

(72) Inventors: Gaelle Saintigny, Paris (FR); Christian Mahe, Neuilly sur Seine (FR); Lionel Larue, Bures sur Yvette (FR); Florian Rambow, Antony (FR)

(73) Assignees: CHANEL PARFUMS BEAUTE, Neuilly sur Seine (FR); INSERM (INSTITUT NATIONAL DE LA SANTE ET DE LA RECHERCHE MEDICALE, Paris (FR); INSTITUT CURIE, Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 23 days.

(21) Appl. No.: 14/366,767

(22) PCT Filed: Dec. 18, 2012

(86) PCT No.: PCT/FR2012/052977
§ 371 (c)(1),
(2) Date: Jun. 19, 2014

(87) PCT Pub. No.: WO2013/093329
PCT Pub. Date: Jun. 27, 2013

(65) Prior Publication Data
US 2015/0010485 A1 Jan. 8, 2015

(30) Foreign Application Priority Data
Dec. 19, 2011 (FR) .................................. 11 61950

(51) Int. Cl.
| | |
|---|---|
| *A61K 8/60* | (2006.01) |
| *A61Q 19/02* | (2006.01) |
| *C12N 15/113* | (2010.01) |
| *C12Q 1/66* | (2006.01) |
| *G01N 33/50* | (2006.01) |
| *C12N 15/11* | (2006.01) |
| *C12Q 1/68* | (2006.01) |

(52) U.S. Cl.
CPC .............. *C12N 15/113* (2013.01); *A61K 8/606* (2013.01); *A61Q 19/02* (2013.01); *C12N 15/111* (2013.01); *C12N 15/1137* (2013.01); *C12Q 1/66* (2013.01); *C12Q 1/6883* (2013.01); *G01N 33/5023* (2013.01); *G01N 33/5044* (2013.01); *A61K 2800/74* (2013.01); *A61K 2800/86* (2013.01); *C12N 2310/141* (2013.01); *C12N 2320/30* (2013.01); *C12Q 2600/142* (2013.01); *C12Q 2600/148* (2013.01); *C12Q 2600/178* (2013.01); *G01N 2500/10* (2013.01)

(58) Field of Classification Search
CPC ...................................................... A61K 8/606
See application file for complete search history.

(56) References Cited

FOREIGN PATENT DOCUMENTS

WO    2010/022166 A2    2/2010
WO    2011/063455 A1    6/2011

OTHER PUBLICATIONS

Lei et al. (Analytical Biochemistry, 305, pp. 260-268, Published 2002).*
Wu et al. (Clinical, Cosmetic and Investigational Dermatology, pp. 19-35, Published 2008).*
X. Chen et al.: "Epigenetics, MicroRNAs, and Carcinogenesis: Functional Role of Mi croRNA-137 in Uveal Melanoma", Investigative Ophthalmology & Visual Science, vol. 52, No. 3, Mar. 2, 2011 , pp. 1193-1199, XP055033845, ISSN: 0146-0404, 001: 10.1167/iovs.I0-5272 abstract.
L. T. Bemis et al.: "MicroRNA-137 Targets Microphthalmia-Associated Transcription Factor in Melanoma Cell Lines". Cancer Research, vol. 68. No. 5. Mar. 3, 2008 , pp. 1362-1368. XP055033767, ISSN:0008-5472, DOI:10.1158/0008-5472.CAN-07-2912 cited in the application abstract p. 1363. left-hand column. paragraph 1 p. 1367. left-hand column. paragraph 2—right-hand column. paragraph 2.
David TS Wu et al. "Mir-434-5p mediates skin whitening and lightening", Clinical Cosmetic and Investigational Dermatology, vol. 1. Oct. 7, 2008. pp. 19-35. XP055033796, cited in the application abstract.
Lin Shi-Lung et al.: "Chapter 4: Recent Application of Intronic MicroRNA Agents in Cosmetics", 2008. Current Perspectives in MicroRNAs (MIRNA). Springer Netherlands. NL. pp. 51-72, XP009136584, ISBN: 978-1-4020-8532-1 abstract p. 63. paragraph 1—p. 69. paragraph 1.
Mueller D W et al.: "miRNA expression profiling in melanocytes and melanoma cell lines reveals miRNAs associated with formation and progression of malignant melanoma", Journal of Investigative Dermatology, Nature Publishing Group. GB. vo 1. 129. No. 7. Feb. 12, 2009. pp. 1740-1751. XP002598392, ISSN: 0022-202X. DOI: 10.1038/JID.2008.452 [retrieved on Feb. 12, 2009] abstract p. 1749. right-hand column. paragraph 1-2.
Elsner Peter: "Cosmeceuticals: Drugs vs. Cosmetics" Jun. 15, 2000, Marcel Dekker, Inc .• New York, Basel. XP002680865, ISBN: 0824703057 pp. 129, 130 pages 133-137.
International Search Report, dated Apr. 12, 2013, from corresponding PCT application, PCT/FR2012/052977.

* cited by examiner

*Primary Examiner* — Alma Pipic
(74) *Attorney, Agent, or Firm* — Young & Thompson

(57) ABSTRACT

At least one microRNA selected from among hsa-miR-330, hsa-miR-7 and hsa-miR-137, the mature forms thereof, and the precursors thereof, for depigmenting the skin, and an in vitro method for identifying depigmenting compounds, which includes the steps of: a) placing at least one test compound in contact with a sample of melanocytes; b) measuring the expression or activity of at least one microRNA selected from among miR-330, miR-7 and miR-137, the mature forms thereof, and the precursors thereof, in the melanocytes; c) selecting the compounds for which at least 20% activation of the expression or of the activity of at least one of the microRNAs is measured in the melanocytes treated in a) by an element for comparing with the untreated melanocytes.

7 Claims, 6 Drawing Sheets

```
                         SEQUENCE LISTING

<160> NUMBER OF SEQ ID NOS: 20

<210> SEQ ID NO 1
<211> LENGTH: 22
<212> TYPE: RNA
<213> ORGANISM: Homo sapiens

<400> SEQUENCE: 1
ucucugggcc ugugucuuag gc                                          22

<210> SEQ ID NO 2
<211> LENGTH: 23
<212> TYPE: RNA
<213> ORGANISM: Homo sapiens

<400> SEQUENCE: 2
uggaagacua gugauuuugu ugu                                         23

<210> SEQ ID NO 3
<211> LENGTH: 23
<212> TYPE: RNA
<213> ORGANISM: Homo sapiens

<400> SEQUENCE: 3
uuauugcuua agaauacgcg uag                                         23

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cacgaaccac ggcactgatt                                             20

<210> SEQ ID NO 5
<211> LENGTH: 22
<212> TYPE: DNA
<213> ORGANISM: Artificial Sequence
```

<220> FEATURE:
<223> OTHER INFORMATION: primer

<400> SEQUENCE: 5
ttttcttgct gccagtctgg ac                                                22

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tggttccttt tataccactg                                                   20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
cagatccgac tcgcttgttc c                                                 21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ttgtaacagc accgaggatg g                                                 21

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
actgagcgac atcctgtggt tc                                                22

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gctcatcggc tgttggtatt g                                                 21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cactttgctg tcccgatgat c                                                 21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
accgtctctc actggattgg                                           20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tacttggtgg ggttttcgag                                           20

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
aaactagcgg ccgctgtcca ggttcccaga gaatatctgc tt                  42

<210> SEQ ID NO 15
<211> LENGTH: 46
<212> TYPE: DNA
<213> ORGANISM: Artificial Sequence
<220> FEATURE:
<223> OTHER INFORMATION: primer

<400> SEQUENCE: 15
ctagaagcag atattctctg ggaacctgga cagcggccgc tagttt              46

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
aaactagcgg ccgctgtcca ggttagctgt caatatctgc tt                  42

<210> SEQ ID NO 17
<211> LENGTH: 46
<212> TYPE: DNA
<213> ORGANISM: Artificial Sequence
<220> FEATURE:
<223> OTHER INFORMATION: primer

<400> SEQUENCE: 17
ctagaagcag atattgacag ctaacctgga cagcggccgc tagttt              46

<210> SEQ ID NO 18
<211> LENGTH: 23
<212> TYPE: RNA
<213> ORGANISM: Artificial Sequence
<220> FEATURE:
<223> OTHER INFORMATION: primer -continued

```
<400> SEQUENCE: 18
aguaaugucc agguucccag aga                                              23

<210> SEQ ID NO 19
<211> LENGTH: 22
<212> TYPE: RNA
<213> ORGANISM: Artificial Sequence
<220> FEATURE:
<223> OTHER INFORMATION: primer

<400> SEQUENCE: 19
cggauucugu guccgggucu cu                                               22

<210> SEQ ID NO 20
<211> LENGTH: 21
<212> TYPE: RNA
<213> ORGANISM: Artificial Sequence
<220> FEATURE:
<223> OTHER INFORMATION: primer

<400> SEQUENCE: 20
aguaaugucc agguuagcgc a                                                21
```

USE OF MICRORNA MOLECULES TO INFLUENCE SKIN PIGMENTATION

Figure 1:
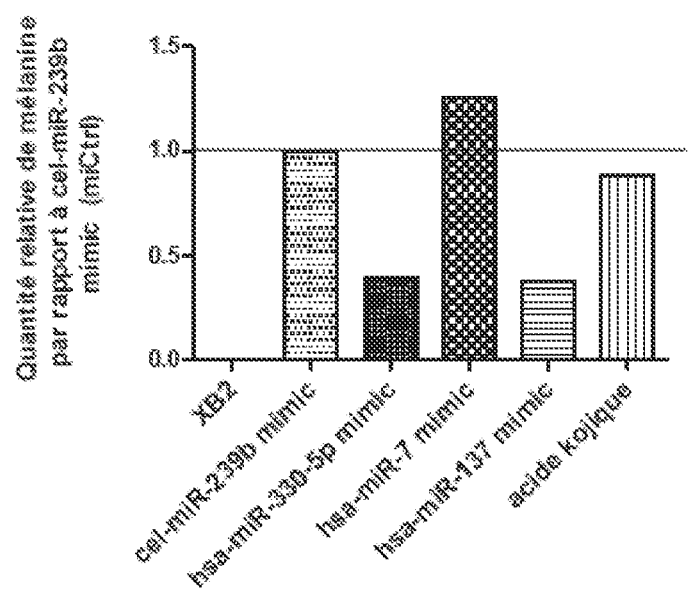

The invention relates to the identification and use of compounds that inhibit the expression or activity of micro-RNAs for influencing the pigmentation of the skin, i.e. for depigmentation or pigmentation of the skin.

The mature micro-RNAs ("miRNAs", also called "miR" in the present application) are small noncoding RNAs (with length of about 21 nucleotides). The miRNAs have been shown to play a role as principal mechanisms of post-transcriptional regulation of gene expression. About 2000 miRNAs have been described in humans (mirBase release 19). They appear to play a role in controlling the activity of more than 60% of all the genes coding for proteins, and participate in the regulation of almost all the cellular processes studied to date (Friedman et al., 2009). In general, the miRNAs inhibit protein synthesis by repressing translation and/or by destabilizing/degrading the mRNAs. miRNA interacts with RNA by an imperfect base complementarity in its "seed" region (sequence of 2-8 nucleotides) at the level of 3'UTR, in the coding region (CDS) or in 5'UTR of the mRNA (Fabian et al., 2010). A mature miRNA can have up to about a hundred mRNA targets. A mature miRNA can be obtained from various miRNA genes situated on various chromosomes in the genome.

The pigmentation process in the melanocytes involves numerous proteins, which could potentially be targeted by the miRNAs. The importance of the miRNAs in the melanocyte lineage has only been studied in the genesis of melanoma. One of the most recent examples published is by Chen et al.: the authors showed that miR-193b represses cellular proliferation and controls cyclin D1 in melanoma (Chen et al., 2010). It has also been shown that Dicer (a key enzyme in the maturation of miRNAs) is essential to permit development of melanoblasts in vivo (Levy et al., 2010). This result shows that the miRNAs are important in the proliferation—at least—of the melanoblasts. To date, just one study has been published on the role of the miRNAs in the pigmentation process (Wu et al., 2008). The authors report that miR-434-5P reduces pigmentation; however, this miR-434-5P has not been found in human public databases. In August 2012, miR-145 has a depigmenting effect on human melanocytes by targeting a protein that is essential for transport of melanosomes (Dynoodt et al., 2012).

The large cohort of miRNAs includes hsa-mir-330, hsa-mir-7 and hsa-mir-137.

The gene of hsa-mir-330 is situated on chromosome 19q13.32, and gives rise to the mature form hsa-miR-330-5p. miR-330 acts as a tumor suppressor in prostate cancer cells by inducing apoptosis via E2F1-mediated suppression of the phosphorylation of AKT (Lee et al., 2009).

As for the mature hsa-miR-7, it can be derived from the three genes hsa-mir-7-1 (Chr. 9q21.32), hsa-mir-7-2 (Chr. 15q26.1), and/or hsa-mir-7-3 (Chr. 19p13.3). miR-7 inhibits the EGFR and AKT pathways, and is inhibited in glioblastoma (Kefas et al., 2008). In carcinoma of the tongue, miR-7 targets IGF1 (Jiang et al., 2010). Introduction of miR-7 in highly invasive breast cancer cells might inhibit their motility, their capacity for invasion and their tumor forming potential by reducing PAK1 (Reddy et al., 2008).

The mature form of hsa-miR-137 comes from the gene of hsa-mir-137 situated on Chr. 1p21.3. hsa-miR-137 targets MITF (Bemis et al., 2008) and the carboxy-terminal binding protein 1 (CtBP1) in a melanoma cell line (Deng et al., 2011). Moreover, hsa-miR-137 induces differentiation of the stem cells of brain cancer (Silber et al., 2008). Furthermore, methylation of the promoter of hsa-mir-137 is associated with poor overall survival of patients with squamous carcinoma of the head and neck (Langevin et al., 2011).

There is therefore a need to find new compounds useful for controlling skin pigmentation, i.e. for depigmentation or pigmentation of the skin.

Notably, there is a need for new depigmenting compounds.

Surprisingly, the inventors identified that the human micro-RNAs hsa-miR-330-5p, hsa-miR-7 and hsa-miR-137 have depigmenting effects on melanocytes.

The present invention therefore relates to the use of at least one micro-RNA selected from hsa-mir-330, hsa-mir-7, hsa-mir-137, their mature forms and their precursors, as depigmenting active ingredient.

The present invention also relates to a micro-RNA selected from hsa-mir-330, hsa-mir-7, hsa-mir-137, their mature forms and their precursors, for use for preventing and/or treating hyperpigmentation disorders.

Preferably, the micro-RNA selected from hsa-mir-330, hsa-mir-7, hsa-mir-137, their mature forms and their precursors, has depigmenting activity when it is used at a concentration between $10^{-7}$ and $10^{-2}$ g/ml.

"micro-RNA precursor" means the premature form or forms of said micro-RNA, and notably their "hairpin or stem loop" forms.

The micro-RNAs according to the invention are preferably of human origin, and are therefore preferably selected from hsa-mir-330, hsa-mir-7, hsa-mir-137, their mature forms and their precursors.

Hsa-mir-330 is accessible under number MI0000803 in the database mirbase.org.

The mature forms of hsa-mir-330 are the forms hsa-miR-330-5p (accessible under number MIMAT0004693 in the database mirbase.org), hsa-miR-330-3p (accessible under number MIMAT0000751 in the database mirbase.org).

The mature form hsa-miR-330-5p of sequence 5'-UCU CUG GGC CUG UGU CUU AGG C-3' (SEQ ID NO: 1) is preferably used.

"hsa-miR-7" means the forms hsa-mir-7-1, hsa-mir-7-2 and hsa-mir-7-3, accessible respectively under numbers MI0000263, MI0000264 and MI0000265 in the database mirbase.org.

The mature forms of hsa-mir-7-1 are the forms hsa-miR-7-5p (accessible under number MIMAT0000252 in the database mirbase.org), hsa-miR-7-1-3p (accessible under number MIMAT0004553 in the database mirbase.org).

The mature forms of hsa-mir-7-2 are the forms hsa-miR-7-5p (accessible under number MIMAT0000252 in the database mirbase.org), hsa-miR-7-2-3p (accessible under number MIMAT0004554 in the database mirbase.org).

The mature form of hsa-mir-7-3 is the form hsa-miR-7-5p (accessible under number MIMAT0000252 in the database mirbase.org).

Also, preferably, since hsa-mir-7-1, 7-2 and 7-3 have a common mature form hsa-miR-7-5p, this last-mentioned of sequence 5'-UGG AAG ACU AGU GAU UUU GUU GU-3' (SEQ ID NO: 2) is used.

Hsa-miR-137 is accessible under number MI0000454 in the database mirbase.org.

The mature form of hsa-mir-137 is the form hsa-miR-137 (accessible under number MIMAT0000429 in the database mirbase.org), of sequence 5'-UUA UUG CUU AAG AAU ACG CGU AG-3' (SEQ ID NO: 3).

The hyperpigmentation disorders according to the invention are preferably selected from melasma, chloasma, lentigines, senile lentigo, irregular hyperpigmentations associated with photoaging, freckles, post-inflammatory hyperpigmentations due to an abrasion or to a burn or to a scar or to a dermatosis or to a contact allergy, nevi, genetically determined hyperpigmentations, hyperpigmentations of metabolic origin or drug-induced, and melanomas.

The present invention also relates to an in vitro method for identifying depigmenting compounds, comprising the following steps:
   a. putting at least one test compound in contact with a sample of melanocytes;
   b. measuring the expression or the activity of at least one micro-RNA selected from hsa-mir-330, hsa-mir-7 and hsa-mir-137, their mature forms and their precursors, in said melanocytes;
   c. selecting the compounds for which at least 20% of activation of the expression or of the activity of at least one of said micro-RNAs, its mature forms and precursors, is measured in the melanocytes treated in a., in comparison with the untreated melanocytes.

According to a first embodiment, step b. is carried out before and after step a. In this case, the expression or the depigmenting activity of the micro-RNA measured in the melanocytes before step a. corresponds to the control value (i.e. the untreated melanocytes). Thus, step c. comprises selecting the compounds for which activation of at least 20%, preferably at least 30%, preferably at least 40% of the expression or of the activity of at least one micro-RNA is measured in the melanocytes treated in a. compared with the same melanocytes before step a.

According to another embodiment, the method comprises a first step a'. of preparing the samples of melanocytes. Thus, preferably, the present invention relates to an in vitro method for identifying depigmenting compounds, comprising the following steps:
   a'. preparing at least two samples of melanocytes;
   a. putting one of the samples in contact with at least one test compound, then
   b. measuring the expression or the activity of at least one micro-RNA selected from hsa-mir-330, hsa-mir-7 and hsa-mir-137, their mature forms and their precursors, in said samples, and
   c. selecting the compounds for which at least 20% of activation of the expression or of the activity of at least one of said micro-RNAs, its mature forms and precursors, is measured in the melanocytes treated in a., in comparison with the untreated melanocytes.

In this second embodiment, the expression or the activity of the micro-RNA or of a mature form or precursor, measured in the sample of melanocytes not submitted to step a., corresponds to the control value (i.e. the untreated melanocytes).

The test compound can be of any type. It can be of natural origin or can have been produced by chemical synthesis. It can be obtained from a bank of structurally defined chemical compounds, or of compounds or substances that have not been characterized, or a mixture of compounds. It can notably be selected from natural compounds, which comprise compounds of vegetable origin, such as plants. Preferably, the test compounds are of vegetable origin; preferably they are selected from botanical extracts.

According to step a., the test compound is put in contact with a sample of melanocytes.

According to step b., the expression and/or the activity of at least one micro-RNA, its mature form or precursors, is measured in the melanocytes. "Expression of a micro-RNA" means the quantity of micro-RNA produced. Expression of the micro-RNA means both during transcription of the gene coding for said micro-RNA, and during maturation of said micro-RNA. "Activity of a micro-RNA" means the depigmenting activity of said micro-RNA, i.e. the capacity of said micro-RNA for inhibiting skin pigmentation, i.e. the capacity of said micro-RNA for reducing the amount of melanin produced by the melanocytes.

A person skilled in the art is familiar with the quantitative or semiquantitative techniques for detecting the mRNA that hybridizes to the micro-RNA, and thus for determining the activity of the micro-RNA. Techniques based on hybridization of the mRNA with specific nucleotide probes are the commonest, such as Northern blot, RT-PCR (reverse transcriptase polymerase chain reaction), quantitative RT-PCR (qRT-PCR).

A person skilled in the art is also familiar with the quantitative or semiquantitative techniques for detecting the micro-RNAs, or the mRNA that hybridizes to the micro-RNA. In particular, the expression of the micro-RNA can be measured by real-time PCR. The activity of the micro-RNA can be measured by real-time PCR on mRNA targets, or by evaluating the level of target proteins by Western blot. Preferably, the expression of the micro-RNA is measured by real-time PCR. Preferably, the activity of the micro-RNA is measured by quantifying the amount of melanin produced.

The expression or the activity of the micro-RNA after treatment with the test compound is then compared to a control value, i.e. a value obtained in the same melanocytes before the treatment, or a value obtained in another sample of melanocytes that have not been treated.

According to step c, the compounds that can be used are those for which activation of at least 20%, preferably at least 30%, preferably at least 40% of the expression or of the activity of at least one micro-RNA is measured in the treated melanocytes relative to the untreated melanocytes. Preferably, the activation of the expression or of the activity of the micro-RNAs is at least 50%, preferably at least 60%.

The compounds selected by means of the methods of screening defined in the invention can then be tested on other models in vitro and/or in models in vivo for their effects on skin pigmentation. The compounds useful according to the invention are activators of the targeted micro-RNAs.

According to another embodiment, the present invention relates to an in vitro method for identifying propigmenting compounds, comprising the following steps:
   a. putting at least one test compound in contact with a sample of melanocytes;
   b. measuring the expression or the activity of at least one inhibitor of hsa-miR-330-5p, hsa-miR-7 and/or hsa-miR-137 (for example antagomir), their mature forms, in said melanocytes;
   c. selecting the compounds for which at least 20% inhibition of the expression or activity of at least one of said micro-RNAs, its mature forms and precursors, is measured in the melanocytes treated in a., in comparison with the untreated melanocytes.

In this case, the compounds selected in step c) are compounds that are inhibitors of micro-RNAs. The inhibitor can be an antisense DNA, an RNA or an siRNA. Preferably, the inhibitors of micro-RNAs are anti-miRs. The anti-miRs are inhibitors of miRs that specifically inhibit the endogenous micro-RNAs. The anti-miRs are single-stranded nucleic acids designed to bind specifically to molecules of micro-RNAs and inhibit them. The anti-miRs have a nucleic acid sequence complementary to the sequence of the target miR. These inhibitors can be introduced into the cells using transfection or electroporation, in a manner similar to that used for the siRNAs. Using anti-miRs, it is possible to perform a functional analysis of the miR by negative regulation of its activity. The anti-miRs are commercially available, and can be obtained for example from Ambion or Applied Biosystems.

The miRs, the miR activators or the miR inhibitors identified using the methods of screening described above can be formulated in a composition, in combination with a physiologically acceptable vehicle, preferably a cosmetically acceptable medium, i.e. a medium that is suitable for use in contact with human skin, without any risk of toxicity, incompatibility, instability or allergic reaction and especially that does not cause sensations of discomfort (redness, tightness, tingling, etc.) that are unacceptable to the user. These compositions can be administered, for example, orally or topically. Preferably, the composition is applied topically. For the oral route, the composition can be in the form of tablets, capsules, sugar-coated tablets, syrups, suspensions, solutions, powders, granules, emulsions, suspensions of microspheres or nanospheres or lipid or polymer vesicles for controlled release. For the topical route, the composition is more particularly intended for treating the skin and the mucosae and can be in the form of ointments, creams, milks, ointments, powders, impregnated buffers, solutions, gels, sprays, lotions or suspensions. It can also be in the form of suspensions of microspheres or nanospheres or lipid or polymer vesicles or polymer patches or hydrogels allowing controlled release. This composition for topical application can be in anhydrous form, in aqueous form or in the form of an emulsion. The composition for topical application can be in the form of an oil-in-water, water-in-oil or multiple (W/O/W or O/W/O) emulsion, which can optionally be microemulsions or nanoemulsions, or in the form of an aqueous dispersion, a solution, an aqueous gel or a powder. In a preferred variant, the composition is in the form of a gel, a cream or a lotion.

The physiologically acceptable vehicle of the composition generally comprises water and optionally other solvents such as ethanol.

This composition is preferably used as a care product and/or cleaning product for the skin of the face and/or of bodily lesions, and it can notably be in the form of a liquid, a gel or a mousse, packaged for example in a pump-action spray bottle, an aerosol or a tube, or in the form of cream packaged for example in a jar. As a variant, it can be in the form of a makeup product and in particular a foundation or a loose or compacted powder.

It can comprise various additives, such as at least one compound selected from:
  oils, which can notably be selected from the volatile or nonvolatile, linear or cyclic silicone oils, such as the polydimethylsiloxanes (dimethicones), polyalkylcyclosiloxanes (cyclomethicones) and polyalkylphenylsiloxanes (phenyl dimethicones); the synthetic oils such as fluorinated oils, the alkyl benzoates and the branched hydrocarbons such as polyisobutylene; vegetable oils and in particular soybean oil or jojoba oil and mineral oils such as liquid paraffin;
  waxes such as ozokerite, polyethylene wax, beeswax or carnauba wax;
  silicone elastomers obtained notably by reaction, in the presence of a catalyst, of a polysiloxane containing at least one reactive group (notably hydrogen or vinyl) and bearing at least one alkyl group (notably methyl) or phenyl group, in an end position and/or side position, with an organosilicone such as an organohydrogen polysiloxane;
  surfactants, preferably emulsifying surfactants whether nonionic, anionic, cationic or amphoteric, and in particular the esters of a fatty acid and a polyol such as the esters of fatty acid and of glycerol, the sorbitan fatty acid esters, the esters of fatty acids and of polyethylene glycol and the sucrose fatty acid esters; polyethylene glycol fatty alcohol ethers; alkylpolyglucosides; modified polysiloxane-polyethers; betaine and derivatives thereof; polyquaterniums; alkyl sulfate salts; sulfosuccinates; sarcosinates; alkyl and dialkyl phosphates, and their salts, and soaps of fatty acids;
  co-surfactants such as the linear fatty alcohols and in particular cetyl alcohol and stearyl alcohol;
  thickeners and/or gelling agents, and in particular crosslinked or noncrosslinked, hydrophilic or amphiphilic homopolymers, and copolymers, AMPS and/or polymers of acrylamide and/or of acrylic acid and/or salts of acrylic acid or esters; xanthan gum or guar gum, cellulose derivatives, and silicone gums (dimethiconol);
  organic filters, such as the derivatives of dibenzoylmethane, derivatives of cinnamic acid, the salicylates, para-aminobenzoic acids, β, β'-diphenyl acrylates, benzophenones, benzylidene derivatives, phenyl benzimidazoles, triazines, phenyl benzotriazoles and anthranilic derivatives;
  inorganic filters, based on mineral oxides in the form of coated or uncoated pigments, or nanopigments, and in particular based on titanium dioxide or zinc oxide;
  colorants;
  preservatives;
  sequestering ingredients such as the salts of EDTA;
  perfumes;
  and mixtures thereof, this list not being exhaustive.

Examples of these additives are mentioned in particular in the CTFA dictionary (International Cosmetic Ingredient Dictionary and Handbook published by Les cosmétiques, produits de toilette et parfums, 11th edition, 2006), which describes a great variety, without limitation, of cosmetic and pharmaceutical ingredients generally used in the skin care industry, which are suitable for use as additional ingredients in the compositions according to the present invention.

The composition can also comprise at least one optical-effect compound, such as fillers, pigments, nacres, lifting agents and polymers, and mixtures thereof.

The "fillers" are colorless or white, mineral or synthetic, lamellar or nonlamellar, and are suitable for giving the composition stiffness and/or softness, a matte effect and/or uniformity. As fillers, we may notably mention talc, mica, silica, kaolin, powders of Nylon® such as Nylon-12 (Orgasol® marketed by the company Atochem), polyethylene powders, polyurethane powders, polystyrene powders, polyester powders, microbeads of silicone resin such as those sold by the company Toshiba under the name Tospearl®, hydroxyapatite, and hollow silica microspheres (Silica Beads® from the company Maprecos).

The term "pigments" is to be understood as white or colored, mineral or organic particles that are insoluble in the medium, which are intended to color and/or opacify the composition. They can be of usual size or nanometric. Among the mineral pigments, we may mention titanium dioxide, zirconium oxide, cerium dioxide, zinc oxide, iron oxide and chromium oxide.

The term "nacres" is to be understood as iridescent particles that reflect the light. Among the nacres that may be envisaged, we may mention natural resources such as pearls, mica covered with titanium oxide, iron oxide, natural pigment or with bismuth oxychloride, and colored titanium mica.

The concentration by weight of these fillers and/or pigments and/or nacres in the aqueous phase is generally from 0.1% to 20% and preferably from 0.2% to 7% by weight relative to the total weight of the composition.

"Lifting agent" is to be understood as meaning a suitable compound for making the skin taut. By means of this effect of tautness, it makes the skin smooth and immediately reduces or even eliminates wrinkles and lines. Among the lifting agents, we may notably mention the polymers of natural origin. The term "polymers of natural origin" signifies polymers of vegetable origin, polymers derived from integuments, egg proteins and latices of natural origin. These polymers are preferably hydrophilic. Among the polymers of vegetable origin, we may notably mention the proteins and the protein hydrolysates, and more particularly extracts of cereals, of leguminous plants and of oleaginous plants, such as extracts of maize, of rye, of wheat, of buckwheat, of sesame, of spelt, of pea, of beans, of lentils, of soya and of lupine. The synthetic polymers are generally in the form of a latex or a pseudo and can be of the polycondensate type or those obtained by radical polymerization. We may mention in particular the polyester/polyurethane and polyether/polyurethane dispersions. Preferably, the lifting agent is a copolymer of PVP/dimethiconyl acrylate and of hydrophilic polyurethane (Aquamere S 2001® from the company HYDROMER).

It is also possible to use polymers in solution, in dispersion or in the form of particles, which reduces the sheen of the skin and makes the complexion more uniform. Examples that may be mentioned comprise the silicone elastomers; resin particles, and mixtures thereof. As examples of silicone elastomers, we may mention the products marketed under the name KSG® by the company Shin-Etsu, under the name Trefil®, BY29® or EPSX® by the company Dow Corning or under the names Gransil® by the company Grant Industries.

The composition used according to the invention can also comprise active agents other than the micro-RNA or its activator, and in particular at least one active ingredient selected from:
  agents that stimulate the production of growth factors;
  anti-glycation agents, agents that increase the synthesis of collagen or prevent its degradation (anti-collagenase agents and in particular inhibitors of matrix metalloproteinases), agents that increase the synthesis of elastin or prevent its degradation (anti-elastase agents);
  agents that stimulate the synthesis of integrin or of the constituents of focal adhesion, such as tensin;
  agents that increase the synthesis of glycosaminoglycans or of proteoglycans or that prevent their degradation (anti-proteoglycanase agents);
  agents that increase the proliferation of fibroblasts;
  depigmenting or antipigmenting agents;
  antioxidants or anti-free radical agents or antipollution agents, and mixtures thereof, this list not being exhaustive.
  Examples of such agents are notably:
  extracts of plants and in particular the extracts of *Chondrus crispus*, of *Thermus thermophilus*, of *Pisum sativum* (Proteasyl® TP LS), of *Centella asiatica*, of *Scenedesmus*, of *Moringa pterygosperma*, of *hamamelis*, of *Castanea sativa*, of *Hibiscus sabdriffa*, of *Polianthes tuberosa*, of *Argania spinosa*, of aloe vera, of *Narcissus tarzetta*, or of licorice;
  an essential oil of *Citrus aurantium* (Neroli);
  the α-hydroxy acids such as glycolic acid, lactic acid and citric acid, and esters;
  the β-hydroxy acids such as salicylic acid and derivatives thereof;
  hydrolysates of vegetable proteins (especially of soya or of hazelnut);
  the acylated oligopeptides (notably marketed by the company SEDERMA under the trade names Maxilip®, Matrixyl® 3000, Biopeptide® CL or Biopeptide® EL);
  extracts of yeast and especially of *Saccharomyces cerevisiae;*
  extracts of algae and especially of Laminaria;
  vitamins and derivatives thereof such as ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate;
  arbutin, kojic acid, ellagic acid, and mixtures thereof.

As a variant or in addition, the composition used according to the invention can comprise at least one elastase inhibitor (anti-elastase), such as an extract of seeds of *Pisum sativum* that is notably marketed by the company Laboratoires Sérobiologiques/Cognis France under the name Proteasyl TP LS®.

The composition can also contain inert additives or combinations of these additives, such as wetting agents, stabilizers, moisture regulators, pH regulators, osmotic pressure modifiers, or UV-A and UV-B screens.

The following examples illustrate the invention without limiting its scope.

FIG. 1: Relative quantity of melanin in the protein lysates on day 12 relative to miCtrl (cel-miR-239b)

Melanin absorption was measured at 470 nm. The lysate of proteins in the unpigmented cells XB2 serves as calibrator (Abs470 nm=0). The sample miCtrl (cel-miR-239b) is used as reference sample (Abs470 nm=1). The relative levels of melanin show a reduction of the pigmented MNT-1 cells treated with the mimetics of hsa-miR-330-5p (mi-330) and hsa-miR-137 (mi-137) relative to the transfection control (cel-miR-239b). The melanin absorption is also normalized relative to the amount of proteins in each lysate sample.

Figure 2:
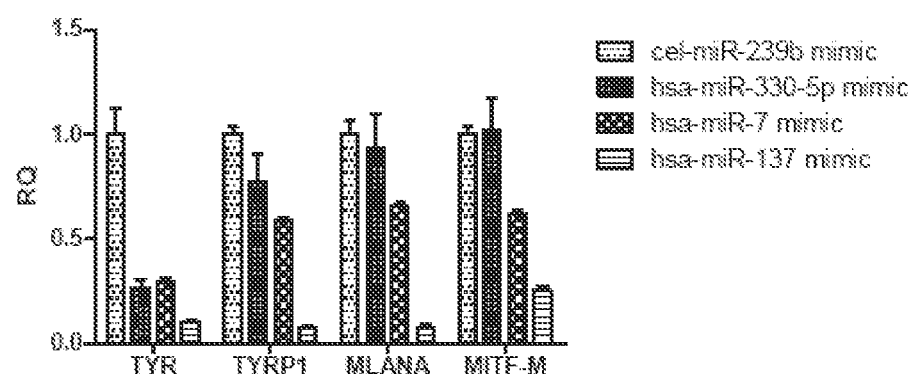

FIG. 2: mRNA expression of genes involved in pigmentation, after treatment with miRNA mimetics (day 12)

Expression of the mRNAs of Tyr, TYRP1, MLANA and MITF-M was measured by PCR-qRT analysis (relative quantification method $\Delta\Delta Ct$). The MNT-1 cells treated with the negative control (cel-miR-239b) served as calibrator sample (relative quantity, RQ=1). Expression of the mRNA of MNT-1 cells treated with the mimetics of hsa-miR-330-5p (mi-330), hsa-miR-7 (mi-7) and hsa-miR-137 (mi-137) is reported as relative value, relative to the calibrator sample. The error bars represent the standard deviation of the measurement in triplicate. The levels of mRNA TYR of the MNT-1 cells are decreased in treatments with mimetics of hsa-miR-330-5p, hsa-miR-7 and hsa-miR-137. The levels of mRNA of TYRP1, MLANA and MITF-M appear to be slightly reduced by miR-7 and considerably reduced by miR-137.

Figure 3:
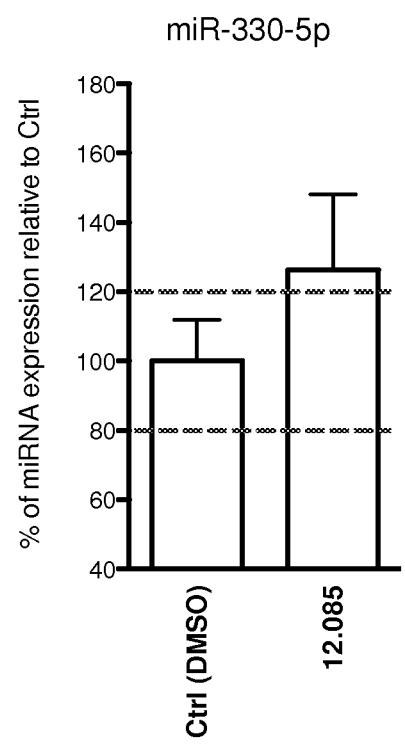

FIG. 3: expression of miR-330-5p after treatment

Expression of miR-330-5p is increased by more than 20% in the MNT-1 cells after treatment with compound 12,085, after 48 h relative to the control. The values are expressed as mean value, and the error bars represent the standard error. *P=0.0233 (unmatched Student t-test)

Figure 4:
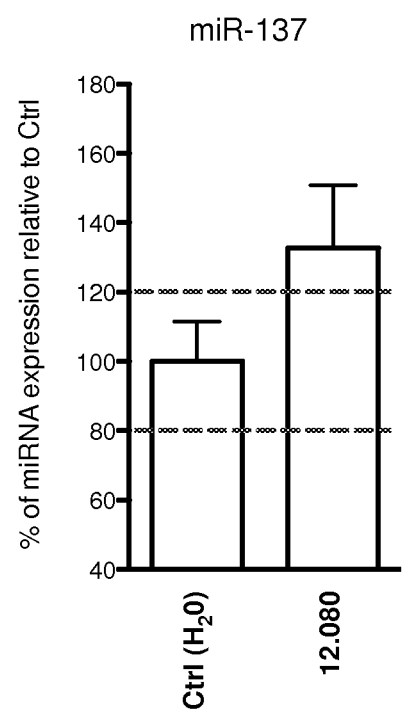

FIG. 4: expression of miR-137 after treatment

Expression of miR-137 is increased by more than 20% in the MNT-1 cells after treatment with compound 12,080, after 48 h relative to the control. The values are expressed as mean value, and the error bars represent the standard error. *P=0.0056 (unmatched Student t-test)

Figure 5:
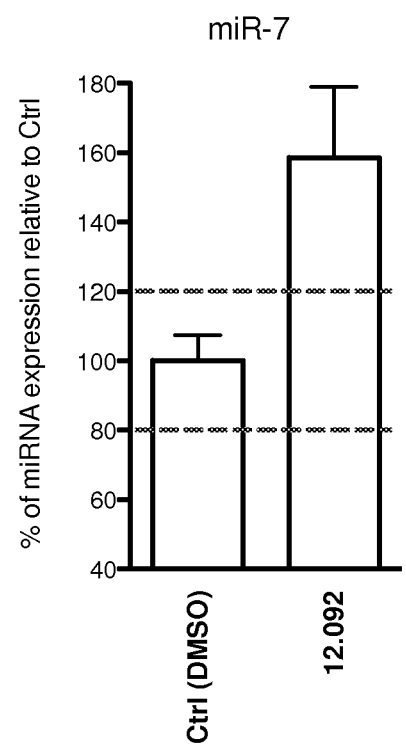

FIG. 5: expression of miR-7 after treatment

Expression of miR-7 is increased by more than 20% in the MNT-1 cells after treatment with compound 12,092, after 48 h relative to the control.

Figure 6:
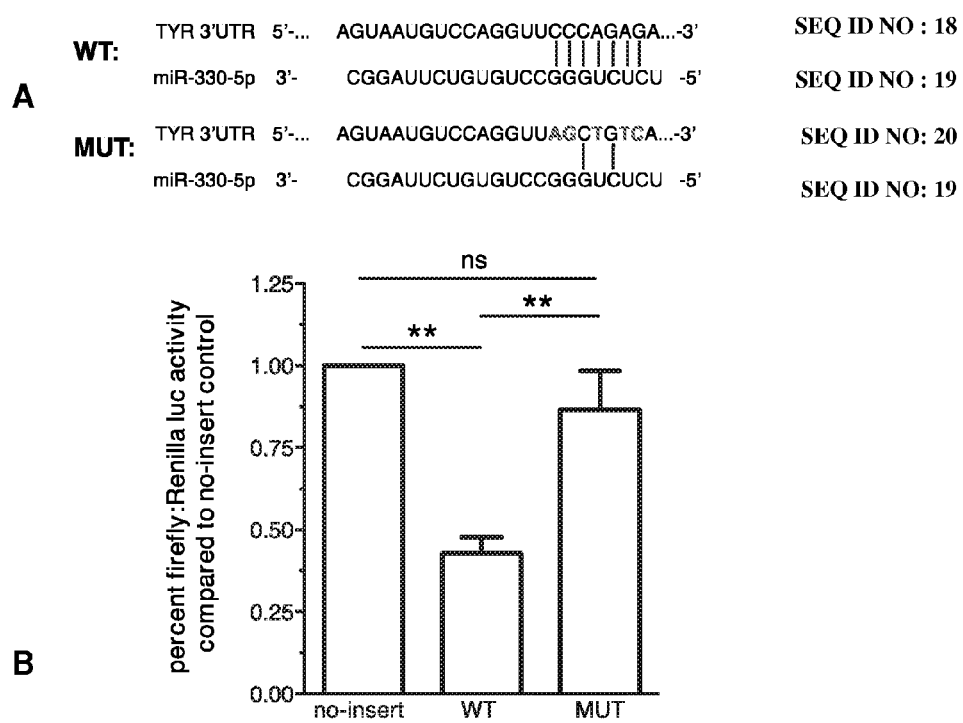

FIG. 6: efficacy of expression of miR-330-5p after treatment

A) Schematic representation of the binding site of miR-330-5p in the 3'UTR portion of tyrosinase (TYR). The wild-type sequence (WT) of the binding site of miR-330-5p is indicated. The mutated sequence (MUT) has 5 nucleotide changes (marked in red).

B) The test of activity of the luciferase reporter shows binding of miR-330-5p to TYR 3'UTR. Lu1205 human melanoma cells were transfected with various luciferase reporter vectors (without insert, WT and MUT) and co-transfected with mimetics of miR-330-5p for 24 h. Luciferase activity is measured on the protein extract obtained from the lysed cells. The construct without insert served as reference. The values are expressed in the form of mean value. The error bars represent the standard deviation. (**P<0.005 Mann-Whitney test).

EXAMPLE 1

Material and Methods

Cells

Human melanoma pigmented cells MNT-1 (Reish et al., 1995) were cultured in RPMI1640 medium (#21875, Gibco), with 10% fetal calf serum (#10270, Gibco), 1% penicillin-streptomycin (#15140, Gibco) and 1% L-glutamine (#25030, Gibco), at 37° C. and 5% $CO_2$ in humid atmosphere. XB2 mouse keratinocytes (Rheinwald and Green, 1975) were cultured in DMEM (#41965, Gibco), with 10% fetal calf serum (#10270, Gibco), 1% penicillin-streptomycin (#15140, Gibco) and 1% L-glutamine (#25030, Gibco), at 37° C. and 5% $CO_2$ in a humidified atmosphere.

Mimetics of the miRNAs and Treatment with Kojic Acid $4 \times 10^5$ MNT-1 cells were seeded per well in a 6-well plate (#353046, Falcon) on day-1. On day 0, the cells were transfected with 50 nM of mimetic of the miRNAs (hsa-mir-137 # C-300604-07-005, hsa-mir-7 # C-300547-05-0005, hsa-mir-330-5p # C-301082-01-0005, negative control # NC-002000-01-05, Dharmacon), using 5 µL of Lipofectamine 2000 (#1668-019, Invitrogen). On day 1, the medium was changed. On day 3, the cells were trypsinized and seeded at $4 \times 10^5$ cells per well. On day 4, the cells were transfected again with 50 nM of mimetic of the miRNAs (see day 0). On day 5, the medium was changed. On day 7, the cells were trypsinized and seeded at $4 \times 10^5$ cells per well. On day 8, the cells were transfected with 50 nM of mimetic of the miRNAs (see day 0). On day 9, the medium was changed. On day 10, the cells were trypsinized and divided into two (from one by six wells to two by six wells). On day 12, one six-well plate was used for lysis of the RNA and the other for lysis of the proteins. As positive control of depigmentation, MNT-1 cells were incubated with 3.5 mM of kojic acid (Sigma K3125-5G) for 12 days. The cells were distributed as described and the kojic acid was renewed with the medium every 4 days. The percentage inhibition of the kojic acid is of the order of 10%.

Treatment with an Inhibitor of miRNA

To study the potential propigmenting effect by inhibition of hsa-miR-7, hsa-miR-137 and hsa-miR-330-5p, $4 \times 10^5$ Lu1205 cells (a human line of unpigmented melanoma cells) were seeded per well in a 6-well plate (#353046, Falcon) on day-1. On day 0, the cells were transfected with 50 nM of respective inhibitors of miRNA (=antagomiR) (hsa-miR-137 # IH-300604-08-0005, hsa-miR-7 # IH-300546-08-0005, hsa-miR-330-5P # IH-301082-02-0005, negative control # EN-002005-01-05, Dharmacon) using 5 µL of Lipofectamine 2000 (#1668-019 Invitrogen). On day 1, the medium was changed. On day 3, the cells were trypsinized and seeded at $4 \times 10^5$ cells per well. On day 4, the cells were transfected once again with 50 nM of inhibitors of miRNA (see day 0). On day 5, the medium was changed. On day 7, the cells were trypsinized and seeded at $4 \times 10^5$ cells per well. On day 8, the cells were transfected with 50 nM of inhibitors of miRNA (see day 0). On day 9, the medium was changed. On day 10, the cells were trypsinized and divided into two (from one by six wells to two by six wells). On day 12, one six-well plate was used for lysis of the RNA and the other for lysis of the proteins.

Extraction of Total RNA and Reverse Transcription

700 µL of Qiazol lysis buffer (Qiagen) was added per well of a six-well dish after washing the cells twice with PBS. The total RNA was isolated using the miRNeasy Mini kit (Qiagen) according to the manufacturer's protocol. The total RNA was eluted in 30 µl of water without RNAse. The concentration of RNA was measured using the NanoVue spectrophotometer (GE Healthcare). 1 µg of total RNA was reverse-transcribed using the MLV RT-Enzyme system (Invitrogen) in 60 µL of reaction to produce the corresponding cDNA.

qRT-PCR

Real-time PCR was performed using the IQ™ SYBR® Green supermix (Biorad) (final reaction volume of 25 µL: 23 µL of Mix Master and 2 µL of cDNA). The thermocycling conditions (Icycler, Biorad) were as follows: 95° C. for 90 s, and 40 cycles at 95° C. for 30 s, 60° C. for 60 s and 95° C. for 10 s. The concentrations of primers and the sequences are given in Table 5 below:

TABLE 5

Primers used for qRT-PCR

| Gene | | Sequence of primers | Concentration |
|------|------|---------------------|---------------|
| TBP | Sense | 5'-CAC GAA CCA CGG CAC TGA TT-3' (SEQ ID NO: 4) | 300 nM |
| | Anti-sense | 5'-TTT TCT TGC TGC CAG TCT GGA C-3' (SEQ ID NO: 5) | |
| TYR | Sense | 5'-TGG TTC CTT TTA TAC CAC TG-3' (SEQ ID NO: 6) | 300 nM |
| | Anti-sense | 5'-CAG ATC CGA CTC GCT TGT TCC-3' (SEQ ID NO: 7) | |
| TYRP1 | Sense | 5'-TTG TAA CAG CAC CGA GGA TGG-3' (SEQ ID NO: 8) | 300 nM |
| | Anti-sense | 5'-ACT GAG CGA CAT CCT GTG GTT C-3' (SEQ ID NO: 9) | |
| MLANA | Sense | 5'-GCT CAT CGG CTG TTG GTA TTG-3' (SEQ ID NO: 10) | 300 nM |
| | Anti-sense | 5'-CAC TTT GCT GTC CCG ATG ATC-3' (SEQ ID NO: 11) | |
| MITF-M | Sense | 5'-ACC GTC TCT CAC TGG ATT GG-3' (SEQ ID NO: 12) | 300 nM |
| | Anti-sense | 5'-TAC TTG GTG GGG TTT TCG AG-3' (SEQ ID NO: 13) | |

The relative quantity was evaluated using the ΔΔCt comparative method. Briefly, this method compares the quantity of expression of the target gene relative to an endogenous control TBP, within a sample for normalizing the expression.

Within a group of samples, a suitable sample is selected as the calibrator sample (miCtrl). Each sample is then compared with a designated reference to give the relative expression of the target gene relative to this reference sample.

Measurement of the Relative Melanin Concentration

On day 12, the cells were washed in PBS twice and lysed in 75 μL/well of a 6-well dish of lysis buffer for the RIPA proteins. The protein lysates were transferred to 1.5-ml Eppendorf tubes and vortexed lightly to homogenize the solution before putting the tube on ice or for storage at −80° C. 2 μL of protein lysate was used for measuring the absorbance of the melanin at 470 nm using the NanoVue spectrophotometer (GE Healthcare). The protein lysate of the unpigmented XB2 keratinocytes was used as calibrator sample (reference=0). To detect the relative quantity of melanin, all the samples were compared with the transfection control sample (miCtrl). The absorbance at 470 nm of the sample miCtrl was fixed at 1 as reference. In addition, the melanin absorption at 470 nm was normalized taking into account the concentration of proteins of each sample relative to miCtrl.

Western Blot

The proteins were extracted from a six-well plate for 30 minutes at 4° C. using 75 μL of radio-immunoprecipitation buffer (RIPA) (1% NP40, 0.5% of sodium deoxycholate, 0.1% SDS in PBS) with protease inhibitors (Roche). The protein lysates were centrifuged at 14000 rpm for 30 min at 4° C. The supernatant was transferred to a 1.5-ml Eppendorf tube that had been precooled and placed on ice. The concentration of proteins was determined with the BCA Protein Assay (ThermoFisher). The proteins (50 μg) were separated on a 10% SDS-polyacrylamide gel and transferred onto Pro-Tron nitrocellulose membranes (Whatman) at 100V for 1 h at room temperature. The membranes were saturated with 5 of skim milk powder in a buffered Tris saline solution (SCT). The membranes were probed with the dilute primary antibody (see below) in 0.5% (v/v) of Tween/SCT (TTBS) overnight, and then submitted to three washings of five minutes each in TTBS. The secondary antibodies were diluted in TTBS 1:10,000 and were applied for 1 h at room temperature. The membranes are then washed three times in TTBS for 10 min each and developed with the SuperSignal WestPico chemiluminescent solution (Thermoscientific) using Amersham Hyperfilm (GE Healthcare).

The primary antibodies used are as follows:
Polyclonal goat anti-Tyr (C-19), SC-7833 (Santa Cruz), diluted to 1/1000
Polyclonal goat anti-Tyrp1 (G-17), SC-10443 (Santa Cruz), diluted to 1/2000
Monoclonal mouse anti-MLANA (A103), SC-20032 (Santa Cruz), diluted to 1/500
Polyclonal rabbit anti-MITF (donated by S. Saule), diluted to 1/1000
Monoclonal mouse anti-β-actin (CA-15), A5441 (Sigma), 1/7500

The secondary antibodies used are as follows:
IgG anti-mouse HRP, W402B (Promega), 1/10,000
Anti-IgG of goat HRP, 705-035-147 (Jackson ImmunoResearch), 1/10,000
IgG anti-rabbit HRP, NA934 (GE Healthcare), 1/10,000

Results

Hsa-miR-330-5p and Hsa-miR-137 Affect the Levels of Pigmentation

MNT-1 cells treated with the mimetics of hsa-miR-330-5p, hsa-miR-137 for 12 days show a significant reduction in the overall pigmentation levels relative to the cells treated with the negative control (photographs not shown). The XB2 keratinocytes serve as control for the unpigmented cells. The photographs of protein lysates on day 12 show that the MNT-1 cells treated with miR-7 do not show any significant effect on the overall pigmentation. As positive control of depigmentation, the MNT-1 cells were treated with kojic acid.

Quantification of the relative levels of melanin, by measuring the absorbance at 470 nm, confirmed the decrease in melanin in the MNT-1 cells treated with the mimetics of hsa-miR-330-5p or hsa-miR-137 (FIG. 1). cel-miR-239b is used as transfection control. At the molecular level, treatment with mimetic of hsa-miR-330-5p decreased the content of TYR proteins, as shown by the Western blot analysis (photographs not shown). Moreover, hsa-miR-330-5p appears to reduce the levels of mRNA TYR (FIG. 2). Treatment with mimetic of hsa-miR-137 reduces the level of protein TYRP1 slightly and eliminates MLANA and MITF (photographs not shown). The expression levels of mRNA of TYR, TYRP1, MLANA and MITF appeared to be significantly reduced by treatment with the mimetic of hsa-miR-137 (FIG. 2).

The inventors conclude from these results that treatment of the MNT-1 cells with antagomiRs directed against hsa-miR-330-5p, hsa-miR-137 and hsa-miR-7 would induce stabilization of the pigment target genes. This stabilization should induce pigmentation.

Hsa-miR-7 Decreases Expression of the Proteins TYR and MITF

MNT-1 cells treated with a mimetic of hsa-miR-7 for 12 days do not show a significant reduction in the overall pigmentation levels relative to the negative control cells (photographs not shown). Quantification of the relative levels of melanin, by measuring the absorbance at 470 nm, suggests a slight increase in melanin in the MNT-1 cells on treatment with mimetic of hsa-miR-7 (FIG. 1). However, at the molecular level, treatment with mimetic of hsa-miR-7 decreases protein expression of TYR and MITF, as shown by Western blot analysis (photographs not shown). Moreover, miR-7 appears to reduce TYR, TYRP1, MLANA and the levels of mRNA MITF-M (FIG. 2).

EXAMPLE 2

Material and Methods

1. Compounds

On day 0 (D0), 150,000 MNT-1 human melanoma cells were seeded in 24-well plates. On D1, the cells were treated with the following compounds biologically in triplicate for 48 h:

| | | |
|---|---|---|
| 12,080 | H$_2$O | 0.08 |
| 12,085 | DMSO | $4 \cdot 10^{-4}$ |
| 12,092 | DMSO | $16 \cdot 10^{-5}$ |
| 12,093 | Ethanol | $4 \cdot 10^{-4}$ |

Where:
12,080=ascorbyl glucoside;
12,085=leukodopachrome, prepared as described in patent application WO 2011/033207;
12,092=diacetylresveratryl thioctate, prepared as described in patent application WO 2006/134282; and
12,093=cetyl tranexamic ester (TXC).

The compounds were freshly prepared in 10% (v/v) stock solutions before obtaining the final dilution in RPMI complete medium (see the cell culture conditions). The medium containing the compounds was vortexed vigorously, before being applied on the cells. Moreover, the MNT-1 cells were treated with DMSO, ethanol and $H_2O$ as control using appropriate quantities. After 48 h, the cells are rinsed with PBS and lysed with 700 μL Qiazol lysis buffer (Qiagen) before storing them at −80° C. The total RNA was extracted using the miRNeasy kit (Qiagen) and eluted in 30 μl of $H_2O$. The concentration of RNA and the ratios 260/280 nm and 260/230 nm were measured using the Nanodrop technology (Thermo Scientific). One μg of total RNA was reverse-transcribed using the miScriptII system (Qiagen) in a total volume of 20 μl. After reverse transcription, 80 μl of $H_2O$ was added to the 20 μl of cDNA. For each qRT-PCR reaction, 2 μl of dilute cDNA served as a model. qRT-PCR was performed in duplicate. Screening was carried out twice on independent dates. For analysis of the qRT-PCR data, an average threshold was calculated for all of the 96-well plates per screen. Multiple control samples DMSO, ethanol (EtOH) and $H_2O$ were averaged and served as calibration samples for the corresponding compounds (ΔΔCt analysis). SCARNA17 was used as reference gene. The expression levels of miRNA of the control samples were set at 100%. An increase or a decrease by at least 20% was regarded as significant. Finally, an unmatched Student t-test was used for testing whether the potential increase or decrease in expression of the miRNAs is significantly higher or lower than 20%.

2. Luciferase Reporter Assay

The predicted binding site of miR-330-5p in the 3'UTR (position 68-75 of 3'UTR with total length of 393nt) of TYR (NM 000372) including the adjacent bases was designed using the following primers, and was cloned into the pmirGLO reporter vector (Promega) downstream of the region coding for firefly luciferase and using the PmeI and XbaI sites.

LL2086:
(SEQ ID NO: 14)
5'-AAACTAGCGGCCGCTGTCCAGGTTCCCAGAGAATATCTGCTT-3'

LL2087:
(SEQ ID NO: 15)
5'-CTAGAAGCAGATATTCTCTGGGAACCTGGACAGCGGCCGCTAGTTT-3'

LL2088:
(SEQ ID NO: 16)
5'-AAACTAGCGGCCGCTGTCCAGGTTAGCTGTCAATATCTGCTT-3'

LL2089:
(SEQ ID NO: 17)
5'-CTAGAAGCAGATATTGACAGCTAACCTGGACAGCGGCCGCTAGTTT-3'

Ligation of the primers LL2086 (sense) and LL2087 (antisense) represents the wild-type (WT) TYR 3'UTR sequence, whereas ligation of the primers LL2088 (sense) and LL2089 (antisense) represents the mutated form of the binding site of the miR-330-Site 5p in the 3'UTR TYR region (MUT). All the constructs were confirmed by sequencing. On D0, 200,000 Lu1205 cells were seeded in 12-well plates. On D1, the Lu1205 cells were transfected with either 30 ng of pmirGLO empty vector (without insert), or 30 ng of WT construct, or 30 ng of MUT construct. At the same time, the cells were co-transfected with 50 nM of mimetic of miR-330-5p (Dharmacon) using Lipofectamine 2000 (Invitrogen). Forty-eight hours after transfection, the cells were collected and analyzed both with firefly luciferase and with Renilla luciferase (included in the pmirGLO vector) using the luciferase double assay (Promega) and a luminometer (Microlumatplus LB96V, Berthold Technologies). Six individual transfection experiments (n=6) were carried out for the three conditions. The values of firefly luciferase were normalized to the values of Renilla luciferase. The relative luciferase activity was calculated, establishing the condition of non-insertion as 1.

Results

1. Compounds

Pigmented MNT-1 human melanoma cells were treated with the compounds and expression of the miRNAs (miR-330-5p, miR-137 and miR-7) was analyzed after 48 h.

miR-330-5p. 12,085 increases expression of miR-330-5p in MNT-1 cells by at least 20% relative to the treated control sample (FIG. 3).

miR-137. 12,080 is capable of inducing expression of miR-137 by 20% in MNT-1 cells (FIG. 4).

miR-7. 12,092 and 12,093 increase expression of miR-7 in MNT-1 cells by at least 20% relative to the treated control sample (FIG. 5).

2. Luciferase Assay

The predicted binding site of miR-330-5p at 3'UTR of tyrosinase was cloned downstream of a luciferase reporter vector (WT). In addition, a mutated form of the binding site of miR-330-5p (MUT) was cloned (FIG. 6A).

Mechanically, miR-330-5p binds at its expected location and causes degradation of the corresponding mRNA. This degradation of the mRNA is reflected in a decrease in luciferase activity relative to the control not possessing a target for miR-330-5p. When the binding site is mutated, the miRNA can no longer bind and degradation does not take place.

The three constructs were transfected into lines of Lu1205 human melanoma cells, in the presence of mimetics of miR-330-5p. Luciferase activity was considerably reduced for the WT construct relative to the control without insert, which suggests that miR-330-5p binds to the predicted site and induces degradation (FIG. 6B). The mutated form of the binding site of miR-330-5p shows restoration of luciferase activity, suggesting that miR-330-5p can no longer bind effectively to its predicted site and therefore cannot induce degradation.

In conclusion, these results show that miR-330-5p binds directly to its predicted site and degrades the mRNA of tyrosinase.

REFERENCES

Bemis L T, Chen R, Amato C M, Classen E H, Robinson S E, Coffey D G, et al. (2008) MicroRNA-137 targets microphthalmia-associated transcription factor in melanoma cell lines. *Cancer Res* 68:1362-1368.

Chen J, Feilotter H E, Pare G C, Zhang X, Pemberton J G, Garady C, et al. (2010) MicroRNA-193b represses cell proliferation and regulates cyclin D1 in melanoma. *Am J Pathol* 176:2520-2529.

Deng Y, Deng H, Bi F, Liu J, Bemis L T, Norris D, et al. (2011) MicroRNA-137 targets carboxyl-terminal binding protein 1 in melanoma cell lines. *Int J Biol Sci* 7:133-137.

Dynoodt P, Mestdagh P, Van Peer G, Vandesompele J, Goossens K, Peelman L J (2012) Identification of miR-145 as a key regulator of the pigmentary process. *J. Invest. Derm.* doi: 10.1038/jid.2012.266.

Fabian M R, Sonenberg N, Filipowicz W (2010) Regulation of mRNA translation and stability by microRNAs. *Annu Rev Biochem* 79:351-379.

Friedman R C, Farh K K, Burge C B, Bartel D P (2009) Most mammalian mRNAs are conserved targets of microRNAs. *Genome Res* 19:92-105.

Jiang L, Liu X, Chen Z, Jin Y, Heidbreder C E, Kolokythas A, et al. (2010) MicroRNA-7 targets IGF1R (insulin-like growth factor 1 receptor) in tongue squamous cell carcinoma cells. *Biochem J* 432:199-205.

Kefas B, Godlewski J, Comeau L, Li Y, Abounader R, Hawkinson M, et al. (2008) microRNA-7 inhibits the epidermal growth factor receptor and the Akt pathway and is downregulated in glioblastoma. *Cancer Res* 68:3566-3572.

Langevin S M, Stone R A, Bunker C H, Lyons-Weiler M A, Laframboise W A, Kelly L, et al. (2011) MicroRNA-137 promoter methylation is associated with poorer overall survival in patients with squamous cell carcinoma of the head and neck. *Cancer* 117:1454-1462.

Lee K H, Chen Y L, Yeh S D, Hsiao M, Lin J T, Goan Y G, et al. (2009) MicroRNA-330 acts as tumor suppressor and induces apoptosis of prostate cancer cells through E2F1-mediated suppression of Akt phosphorylation. *Oncogene* 28:3360-3370.

Levy C, Khaled M, Robinson K C, Veguilla R A, Chen P H, Yokoyama S, et al. (2010) Lineage-specific transcriptional regulation of DICER by MITF in melanocytes. *Cell* 141: 994-1005.

Reddy S D, Ohshiro K, Rayala S K, Kumar R (2008) MicroRNA-7, a homeobox D10 target, inhibits p21-activated kinase 1 and regulates its functions. *Cancer Res* 68:8195-8200.

Reish O, Townsend D, Berry S A, Tsai M Y, King R A (1995) Tyrosinase inhibition due to interaction of homocyst(e)ine with copper: the mechanism for reversible hypopigmentation in homocystinuria due to cystathionine beta-synthase deficiency. *American journal of human genetics* 57:127-132.

Rheinwald J G, Green H (1975) Formation of a keratinizing epithelium in culture by a cloned cell line derived from a teratoma. *Cell* 6:317-330.

Shirdel E A, Xie W, Mak T W, Jurisica I (2011) NAViGaTing the micronome—using multiple microRNA prediction databases to identify signalling pathway-associated microRNAs. *PLoS One* 6:e17429.

Silber J, Lim D A, Petritsch C, Persson A I, Maunakea A K, Yu M, et al. (2008) miR-124 and miR-137 inhibit proliferation of glioblastoma multiforme cells and induce differentiation of brain tumor stem cells. *BMC Med* 6:14.

Wu D, Chen J S, Chang D C, Lin S L (2008) Mir-434-5p mediates skin whitening and lightening. *Clin Cosmet Investig Dermatol* 1:19-35.

The invention claimed is:

1. An in vitro method for identifying depigmenting compounds, comprising the following steps:
   a. putting at least one test compound in contact with a sample of melanocytes;
   b. measuring the expression or the activity of at least one micro-RNA selected from the group consisting of hsa-mir-330, hsa-mir-7, mature forms thereof and precursors thereof, in said melanocytes;
   c. selecting the at least one test compound for which at least 20% of activation of the expression or of the activity of at least one of said micro-RNA, is measured in the melanocytes treated in a., in comparison with untreated melanocytes.

2. The method as claimed in claim 1, wherein step b. is carried out before and after step a.

3. The method as claimed in claim 1, comprising the following steps:
   a'. preparing at least two samples of melanocytes;
   a. putting one of the samples in contact with at least one test compound, then
   b. measuring the expression or the activity of at least one micro-RNA selected from the group consisting of hsa-mir-330, hsa-mir-7, mature forms thereof and precursors thereof, in said samples, and
   c. selecting the at least one test compound for which at least 20% of activation of the expression or of the activity of at least one of said micro-RNA, is measured in the melanocytes treated in a., in comparison with untreated melanocytes.

4. The method as claimed in claim 1, wherein the expression or activity of at least one micro-RNA selected from the group consisting of hsa-mir-330, hsa-mir-7, mature forms thereof and precursors thereof, is measured by quantification of the corresponding micro-RNA.

5. The method as claimed in claim 1, wherein the at least one test compound is selected from botanical extracts.

6. The method as claimed in claim 1, wherein the melanocytes are obtained from melanoma lines.

7. The method as claimed in claim 6, wherein the melanocytes are obtained from human melanoma lines.

\* \* \* \* \*